(12) United States Patent
Schrepfer et al.

(10) Patent No.: US 7,693,561 B2
(45) Date of Patent: Apr. 6, 2010

(54) METHOD AND DEVICE FOR DETERMINING THE CONCENTRATION OF A SUBSTANCE IN BODY LIQUID

(75) Inventors: Thomas W. Schrepfer, Oberbözberg (CH); Andreas Caduff, Zürich (CH); Etienne Hirt, Cham (CH); Heinz Süsstrunk, Zürich (CH)

(73) Assignee: Solianis Holding AG, Zug (CH)

( * ) Notice: Subject to any disclaimer, the term of this patent is extended or adjusted under 35 U.S.C. 154(b) by 1236 days.

(21) Appl. No.: 09/980,661

(22) PCT Filed: Mar. 6, 2001

(86) PCT No.: PCT/IB01/00334

§ 371 (c)(1),
(2), (4) Date: Oct. 2, 2003

(87) PCT Pub. No.: WO02/069791

PCT Pub. Date: Sep. 12, 2002

(65) Prior Publication Data

US 2004/0065158 A1    Apr. 8, 2004

(51) Int. Cl.
*A61B 5/00* (2006.01)
(52) U.S. Cl. ................................ 600/347; 600/365
(58) Field of Classification Search .............. None
See application file for complete search history.

(56) References Cited

U.S. PATENT DOCUMENTS

| | | | | |
|---|---|---|---|---|
| 4,020,830 A | * | 5/1977 | Johnson et al. ............ 600/348 |
| 4,180,771 A | * | 12/1979 | Guckel ...................... 324/71.1 |
| 4,397,714 A | * | 8/1983 | Janata et al. ............... 205/775 |
| 4,679,426 A | | 7/1987 | Fuller et al. ................... 73/53 |
| 4,765,179 A | | 8/1988 | Fuller et al. ................... 73/53 |
| 4,822,566 A | * | 4/1989 | Newman ................... 422/82.01 |
| 4,875,486 A | | 10/1989 | Rapoport et al. ............ 128/853 |

(Continued)

FOREIGN PATENT DOCUMENTS

AT    395 075 B    9/1992

(Continued)

OTHER PUBLICATIONS

International Search Report for PCT/IB03/05704, mailing date: Mar. 30, 2004.

(Continued)

*Primary Examiner*—Robert L Nasser
(74) *Attorney, Agent, or Firm*—Mintz, Levin, Cohn, Ferris, Glovsky and Popeo, P.C.

(57) ABSTRACT

For measuring the concentration of a substance in body fluid, such as the glucose level in blood or tissue, a strip electrode (18) and a ring electrode (19) are arranged at the specimen. The ring electrode (19) is in direct electrical contact with the specimen while the strip electrode (18) is electrically insulated therefrom. The strip electrode (18) is arranged parallel to an arm or a leg for obtaining a large interaction length. The electrodes (18, 19) form a capacitor in a resonant circuit. A modulated voltage in the MHz range close to or at the resonance frequency is applied to the electrodes and the response of the body fluid is measured. This design allows a measurement of high accuracy.

27 Claims, 4 Drawing Sheets

U.S. PATENT DOCUMENTS

| | | | | |
|---|---|---|---|---|
| 4,965,206 | A | 10/1990 | Kell | 435/291 |
| 5,050,612 | A | 9/1991 | Matsumura | 128/670 |
| 5,077,476 | A | 12/1991 | Rosenthal | 250/341 |
| 5,109,855 | A | 5/1992 | Günter | 128/653.1 |
| 5,353,802 | A | 10/1994 | Ollmar | 128/734 |
| 5,771,891 | A | 6/1998 | Gozani | 128/635 |
| 5,792,668 | A | 8/1998 | Fuller et al. | 436/149 |
| 5,804,967 | A | 9/1998 | Miller et al. | 324/314 |
| 5,890,489 | A | 4/1999 | Elden | 128/898 |
| 6,028,433 | A | 2/2000 | Cheiky-Zelina et al. | 324/663 |
| 6,182,504 | B1 | 2/2001 | Gaisford | 73/61.43 |
| 6,309,884 | B1 | 10/2001 | Cooper et al. | 436/14 |
| 6,320,393 | B1 | 11/2001 | Yasui et al. | 324/663 |
| 6,517,482 | B1 * | 2/2003 | Elden et al. | 600/309 |
| 6,565,509 | B1 | 5/2003 | Say et al. | 600/365 |
| 6,723,048 | B2 | 4/2004 | Fuller | 600/365 |
| 6,954,662 | B2 | 10/2005 | Freger et al. | 600/316 |
| 2002/0106709 | A1 | 8/2002 | Potts et al. | 435/14 |
| 2002/0155615 | A1 | 10/2002 | Novikov et al. | 436/149 |
| 2003/0153821 | A1 | 8/2003 | Berner et al. | 600/345 |
| 2004/0104736 | A1 | 6/2004 | Cohen et al. | 324/692 |
| 2004/0133353 | A1 | 7/2004 | Geutebrück | 702/19 |
| 2004/0147819 | A1 | 7/2004 | Caduff et al. | 600/316 |
| 2004/0240512 | A1 | 12/2004 | Pesach | 374/43 |
| 2005/0101842 | A1 | 5/2005 | Suda | 600/300 |
| 2005/0113662 | A1 | 5/2005 | Djennati et al. | 600/407 |

FOREIGN PATENT DOCUMENTS

| | | |
|---|---|---|
| DE | 30 17 168 A1 | 11/1981 |
| DE | 44 46 346 A1 | 6/1996 |
| DE | 100 35 415 A1 | 1/2002 |
| EP | 0 236 434 B1 | 9/1987 |
| EP | 1 092 386 A1 | 4/2001 |
| GB | 2 033 575 A | 5/1980 |
| GB | 2 055 206 A | 2/1981 |
| GB | 1599241 | 9/1981 |
| GB | 2 100 864 A | 1/1983 |
| RU | 2 069 863 C1 | 11/1996 |
| RU | 2073242 C1 | 2/1997 |
| RU | 2088927 C1 | 8/1997 |
| SU | 1698724 A1 | 12/1991 |
| WO | WO 93/18395 | 9/1993 |
| WO | WO 93/18402 | 9/1993 |
| WO | WO 95/04496 | 2/1995 |
| WO | WO 97/39341 | 10/1997 |
| WO | WO 98/09566 | 3/1998 |
| WO | WO 98/04190 | 5/1998 |
| WO | WO 99/44495 | 10/1999 |
| WO | WO 99/39627 | 12/1999 |
| WO | WO 01/26538 | 4/2001 |
| WO | WO 01/36952 A1 | 5/2001 |
| WO | WO 02/062214 A1 | 8/2002 |
| WO | WO 02/069791 A1 | 9/2002 |
| WO | WO 02/073179 A1 | 9/2002 |
| WO | WO 03/017834 A1 | 3/2003 |

OTHER PUBLICATIONS

Choleau et al. *Diabetes*, 51:3263-3273 (2002).
Feldman et al. *Colloid Polymer Sci.*, 270:768-780 (1992).
Feldman et I. *Rev. Sci Instrum.*, 67(9):3208-3216 (1996).
"General Linear Least Squares", *Numerical Recipes in C: the Art of Scientific Computing*, pp. 671-681, 1988-1992, http://www.nr.com.
Khalil, O., *Diabetes Technol. Therap.*, 6(5):660-695 (2004).
Patent Abstracts of Japan for JP 62-083649 (Matsushita Electric Ind. Co. Ltd.) (Apr. 17, 1987).
Patent Abstracts of Japan for JP 9-201337 (Casio Comput Co. Ltd.) (Aug. 5, 1997).
Patent Abstracts of Japan for JP 2000-162176 (Omron Corp.)(Jun. 16, 2000).

* cited by examiner

METHOD AND DEVICE FOR DETERMINING THE CONCENTRATION OF A SUBSTANCE IN BODY LIQUID

TECHNICAL FIELD

The invention relates to a method and a device for determining the concentration of a substance in an in-vitro or in-vivo specimen containing body liquid according to the preamble of the independent claims.

BACKGROUND ART

Radio wave spectroscopy has been known to provide promising potential in the in-vitro and in-vivo determination of the concentration of glucose and other substances in body fluids. In particular, this technology is of substantial interest for the determination of glucose concentration in blood and/or inter- or intracellular liquid. A device for measuring blood level glucose is disclosed in U.S. Pat. No. 5,792,668, where two electrodes are brought into direct contact with the human body and the impedance is measured between them.

Despite its potential, the technology has not yet been used in commercial devices, which is attributed to the limited accuracy of the presently known solutions.

DISCLOSURE OF THE INVENTION

Hence, it is the goal of the invention to provide a method and device that allow to increase the reliability of this type of measurement.

This goal is reached by the independent claims.

In a first aspect of the invention, the first electrode is electrically insulated from the specimen. Hence, the measured parameter does not depend on the surface conditions of the specimen. Rather, the signal is capacitively coupled to the specimen and the measured parameter depends therefore primarily on the conditions within the specimen. The parameter measured in this way can then be converted to the desired concentration, e.g. by using calibration data.

Preferably, at least two electrodes are provided, wherein the modulated voltage is applied between them. By using two electrodes, a defined field can be established within the specimen. For best signals, it has been found advantageous to place the second electrode in electric contact with the specimen.

The measured parameter preferably depends on the electrical impedance at the electrode(s). It has been found that the concentration of various substances, in particular glucose, affects the real or imaginary part of this impedance because it changes the loss and/or dielectric constant of body fluid.

Preferably, the electrode forms part of a resonant circuit, which is operated at or close to its resonance frequency. Under such conditions, a change of the dielectric or loss properties of the specimen leads to substantial shifts in the parameters of the resonant circuit and can therefore be measured with high sensitivity.

A further aspect of the invention is directed to a device particularly suited for in-vivo measurements of the human body. This device comprises an elongate electrode having a width much smaller than its length. A holder is provided to mount the electrode to an arm or a leg with the longitudinal axis of the electrode extending parallel thereto. In this way, a large interaction space is established, which allows to measure the desired concentration with a higher level of accuracy.

The method and device of the present invention has been found to be especially suited for measuring the glucose concentration in body fluid.

BRIEF DESCRIPTION OF THE DRAWINGS

The invention will be better understood and objects other than those set forth above will become apparent when consideration is given to the following detailed description thereof. Such description makes reference to the annexed drawings, wherein.

MODES FOR CARRYING OUT THE INVENTION

Figure 1:
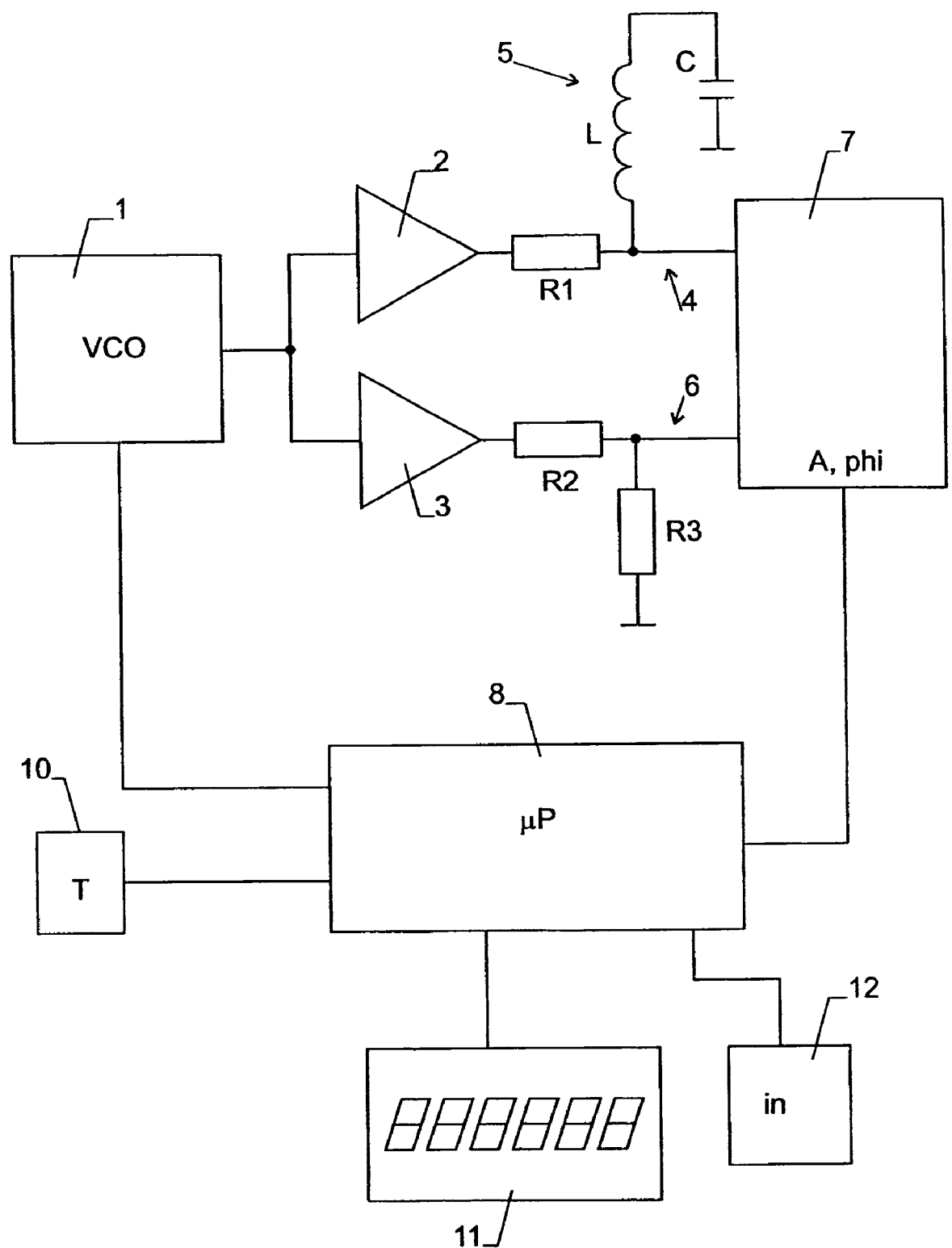
FIG. 1 is a block circuit diagram of a preferred device for carrying out the invention.

FIG. 1 shows a block circuit diagram of a preferred device for carrying out the invention. It comprises a voltage controlled oscillator (VCO) 1 as a signal source for generating a sine wave signal. This signal is fed to two amplifiers 2, 3. The output of first amplifier 2 is connected via a resistor R1 to a first signal path 4. A resonant circuit 5 comprising an inductance L and a capacitor C in series is connected between first signal path 4 and ground. The output of second amplifier 3 is connected via a resistor R2 to a second signal path 56. Second signal path 6 is substantially identical to first signal path 4 but comprises a resistor R3 as a reference load instead of resonant circuit 5.

Both signal paths 4, 6 are fed to a measuring circuit 7, which determines the relative amplitude A of both signals as well as, optionally, their mutual phase shift phi. Relative amplitude A can e.g. be the amplitude of first signal path 4 in units of the amplitude of second signal path 6 (wherein the amplitudes are the peak values of the sine waves).

The output signal of measuring circuit 7 is fed to a microprocessor 8, which also controls the operation of VCO 1.

As can be seen from FIG. 1, the device in the present embodiment further comprises a temperature sensor 10, a display 11 and an input device 12 with user operatable controls, all of which are controlled by microprocessor 8.

Inductance L of the device of FIG. 1 can be generated by a coil and/or by the leads and electrodes of capacitor C. Its value is generally known with reasonable accuracy.

Capacitor C of the device of FIG. 1 is used as an antenna for probing a specimen. For this purpose, it is formed by electrodes that are arranged near the specimen. The geometry of the electrodes is selected such that the electric field generated by them extends into the specimen and the body liquid to be measured. Suitable geometries are discussed below. As mentioned above, at least one of the electrodes of the capacitor is electrically isolated such that capacitor C is primarily a capacitive load, the capacitance and loss of which depends on the electrical properties (i.e. the response) of the specimen at the frequency of VCO 1.

Figure 5:
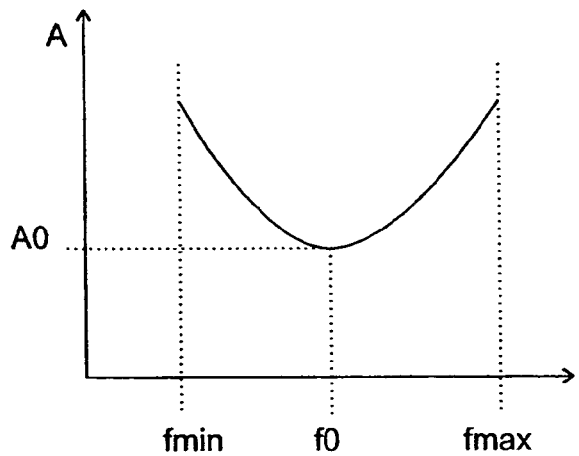
FIG. 5 shows the behavior of the relative amplitude A as a function of frequency.

To measure the concentration of a substance in the body fluid of the specimen, microprocessor 8 can e.g. initiate a measurement cycle consisting of a frequency sweep of VCO 1. The sweep should start at a frequency fmin below the expected resonance frequency f0 of the resonant circuit 5 and extend to a frequency fmax above resonance frequency f. During this sweep, the electrical properties of signal path 4 will change substantially, while those of signal path 6 will vary only slightly. The amplitude determined by measuring circuit A will therefore fall to a minimum A0 at f0, as shown in FIG. 5. At the same time, phase shift phi crosses zero.

As can be shown, the dependence of A0 on the dielectric constant $\epsilon(f)$ and, in particular, on the loss or conductance $\rho(f)$ of the fluid in the specimen is stronger than at off-resonance frequencies, which allows a sensitive measurement of the liquid's response to the electric field.

Figure 8:
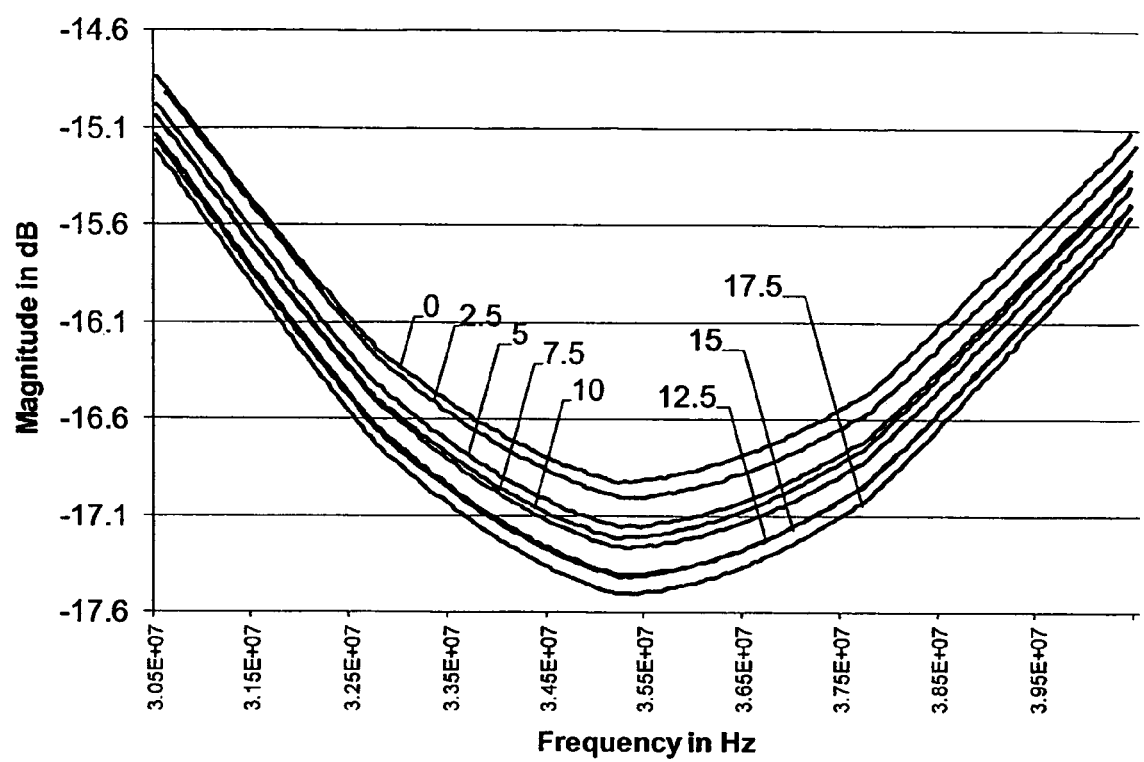
FIG. 8 shows measurements at varying glucose concentrations (mmol/liter) in physiologic solution and FIG. 9 a third embodiment of the circuit.

This is shown in FIG. 8, which represents measurements of the type shown in FIG. 5 at glucose concentrations between 0 and 17.5 mmol/l. The vertical axis represents the ratio in dB of the signals from first signal path 4 and second signal path 6. The resonance frequency is around 35.5 MHz.

It is presently believed that the specific impedance of the body fluid, i.e. the specific conductivity $\rho(f)$ and the dielectric constant $\epsilon(f)$ in a frequency range between 10 MHz and 2000 MHz, and in particular between 20 MHz and 70 MHz, are a function of the properties and concentration of the salty (ionic) components of the human body. These salty components primarily include solvated sodium, potassium, calcium and other minor ions and their counter ions, the primary counter ion being chloride. Other non-ionic solvated substances, in particular substances having a similar range of size as the ion complexes, can have an impact on the impedance pattern of the salty body fluid components, provided these substances occur in sufficient concentration. In particular, glucose has a similar range of size and is present in concentrations giving rise to a well detectable variation of the amplitude A0 at resonance frequency.

In a simple embodiment, only amplitude A0 is measured as a parameter for the determination of the concentration. Suitable calibration data stored in microprocessor 8 is used to convert amplitude A0 into the desired concentration level.

The effects exploited for the measurement are temperature dependent. In order to obtain high accuracy over a wide temperature range, temperature sensor 10 is brought into thermal contact with the specimen to be measured. The signals from temperature sensor 10 are used to correct the obtained result, again using calibration data obtain from calibration measurements.

Figure 2:
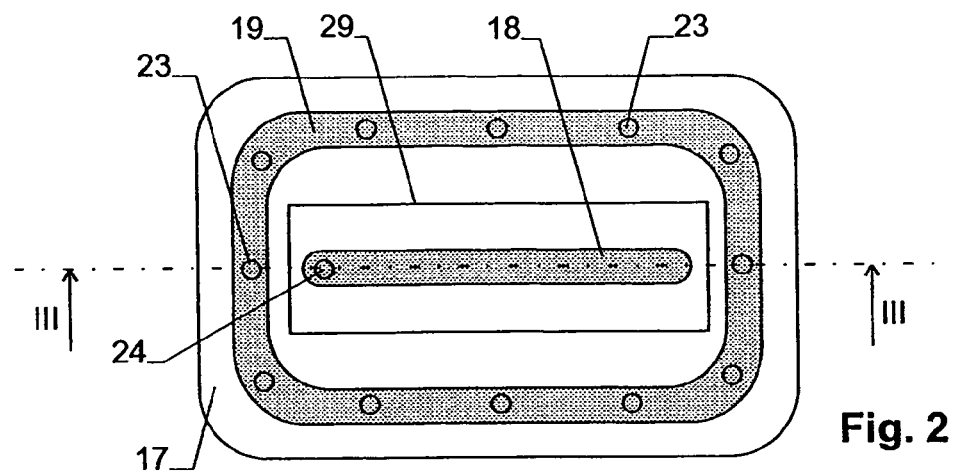
FIG. 2 is a view onto a possible embodiment of the device.
Figure 3:
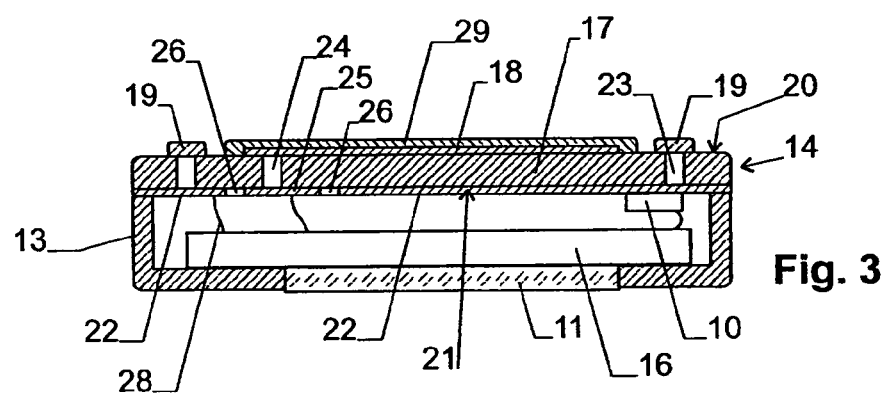
FIG. 3 is a section along line III-III of FIG. 2.

A proper design of the electrodes of capacitor C allows to optimize the accuracy and sensitivity of the present device in a given application. A preferred geometry of the device for in-vivo measurements in a living body is shown in FIGS. 2 and 3.

The device comprises a housing 13 closed on one side by an electrode plate 14. The display 11 is arranged opposite electrode plate 14. The electronic circuits 16 are arranged between electrode plate 14 and display 11.

Electrode plate 14 comprises an electrically insulating substrate 17 with a strip electrode 18 and a top or ring electrode 19 arranged on an outer side 20 thereof. An inner side 21 of insulating substrate 17 is covered by a bottom electrode 22. A plurality of though-contacts 23 are provided to connect ring electrode 19 to bottom electrode 22. A further through-contact 24 connects one end of strip electrode 18 to a small bond pad 25 arranged in an opening 26 of bottom electrode 22 on inner side 21.

Temperature sensor 10 is mounted to bottom electrode 22. The large number of through-contacts 23 ensure that bottom electrode 22 follows the temperature of ring electrode 18 and therefore the temperature of the specimen closely.

A typical size of electrode plate 14 is 32 mm×21 mm. Bottom electrode 22 covers all of inner side 21 except for the small opening 26 and is therefore much larger than strip electrode 18.

Leads 28 are provided to connect bottom electrode 22, contact pad 26 and temperature sensor 10 to the electronic circuits 16.

While bottom electrode 22 and ring electrode 19 are connected to ground, strip electrode 18 is connected to inductance L of resonant circuit 5. Therefore, the capacitor C is formed between strip electrode 18 as a first electrode and ring electrode 19 and bottom electrode 22 as a second electrode. In other words, the second electrode consists of two electrode layers: a top electrode layer formed by ring electrode 19 and a bottom electrode layer formed by bottom electrode 22.

An electrically insulating cover layer 29 covers all of strip electrode 18 but not ring electrode 19. In other words, strip electrode 18 is arranged between substrate 17 and cover layer 29. Cover layer 29 is preferably of a hard, moisture- and salt-impervious material such as glass, ceramics, a polycarbonate or diamond-like carbon (DLC) of a thickness preferably between 50 and 100 μm.

Figure 4:
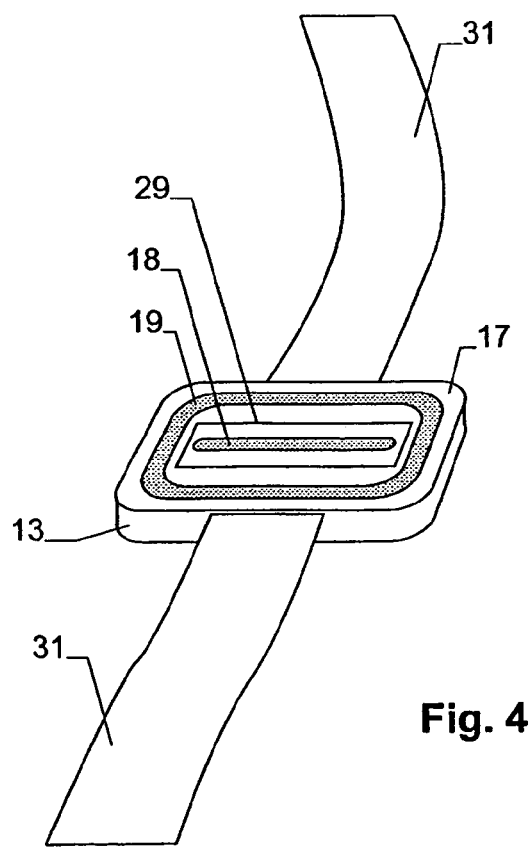
FIG. 4 is the device of FIG. 3 with a wristband.

As can be seen in FIG. 4, a holder or wristband 31 is attached to housing 13 for fixing the device to an arm or a leg of a human body with cover layer 29 facing the body and a longitudinal axis of strip electrode 18 parallel to the arm or leg. In this way, ring electrode 19 comes into contact with the user's skin and sets the same to ground reference potential. The electric field generated by strip electrode 18 extends into the body tissue. Since strip electrode 18 is elongate and has a width much smaller than its length and extends along the arm or leg, a comparatively large region of the body is reached by the field. This allows to obtain more sensitive and accurate measurements.

As described above, a pure sine voltage has been found to be sufficient for obtaining accurate measurements. However, other types for modulated voltages, such as square-wave voltages or pulses can be used as well. In this case, measuring circuit 7 is preferably provided with suitable filters for selectively sampling one or more frequency components. At least one measured frequency component is preferably close to the resonance frequency of resonant circuit 5 for exploiting the circuit's high sensitivity to the specimen's properties at that frequency.

The electrode geometry can be varied for adapting it to a given application. While the design of FIG. 2 is optimized for a measurement on an arm or leg, a circular design can be used for measurement on a flatter body part or an in-vitro sample.

Ring electrode 19 does not necessarily have to form a closed ring as long as it provides sufficient grounding of the body part to be measured. It can e.g. also have U-shape or consist of two stripes parallel to and laterally enclosing strip electrode 18. Ring electrode 19 can also be omitted completely or be covered by cover layer 29, in particular for in-vitro measurements where noise is low.

Figure 6:
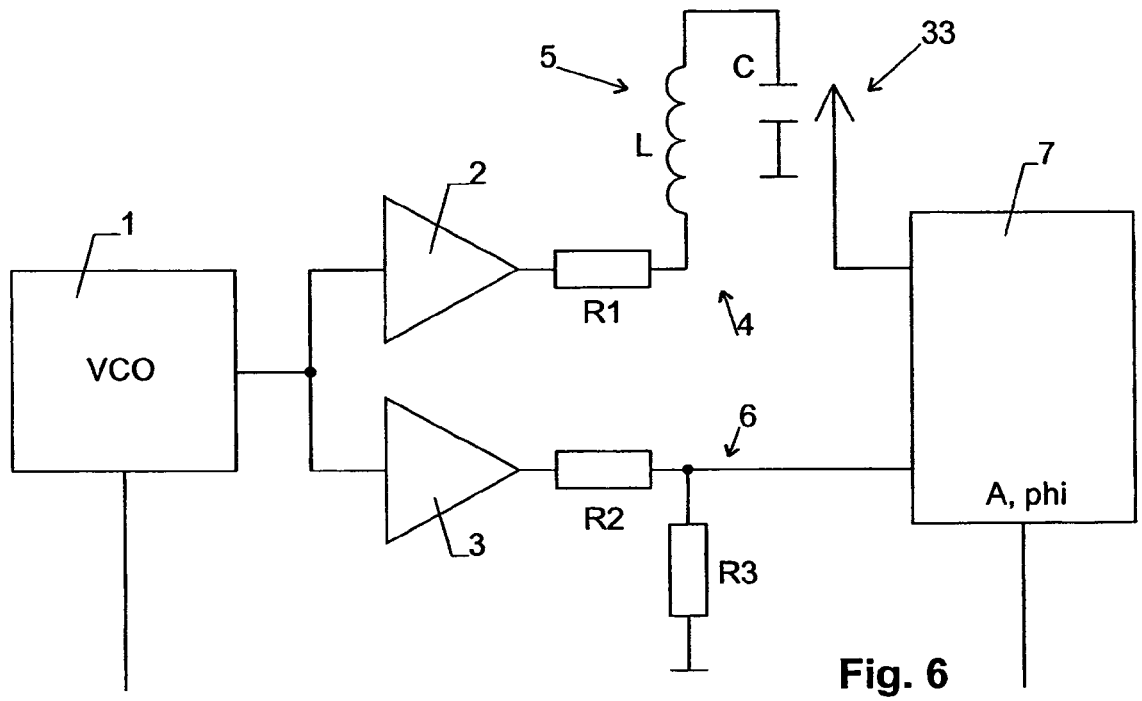
FIG. 6 is a second embodiment of the circuit.

Part of a further embodiment of the circuit is shown in FIG. 6. Here, no direct connection between resonant circuit 5 and measuring circuit 7 is used. Rather, an antenna electrode 33 is located in proximity to the electrodes of capacitor C, and measuring circuit 7 measures the signal returned by antenna electrode 33.

Figure 7:
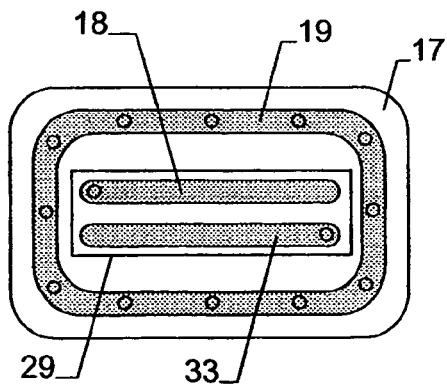
FIG. 7 is an alternative electrode geometry.

A possible arrangement of the electrodes is shown in FIG. 7. As can be seen, antenna electrode 33 is strip shaped and arranged in parallel to strip electrode 18. Both, antenna electrode 33 and strip electrode 18 are covered by cover layer 29 and therefore electrically insulated from the specimen.

The device of FIGS. 6 and 7 is again sweeping VCO 1 between a frequency fmin below the resonance frequency f0 of resonant circuit 5 and a frequency fmax above it. In contrast to FIG. 5, measuring circuit 7 now detects a maximum amplitude A0 at f0, wherein the value of A0 depends on the response, i.e. the electrical properties of the specimen at the resonance frequency f0. The parameter A0 can now again be processed using calibration data as described above.

A comparison of the device of FIGS. 1 and 2 with the device of FIGS. 6 and 7 shows that the first embodiment measures the response of the specimen from the signal reflected to strip electrode 18. The second embodiment measures the response of the specimen from the signal transmitted from strip electrode 18 to antenna electrode 33.

It is found that the transmission and reflection show different dependencies on the concentrations of various compounds of the body fluid. Hence, a combined measurement of reflection and transmission allows a further refinement of the measurement by elimination of the influence of compounds not of interest for the quantity to be measured.

Figure 9:
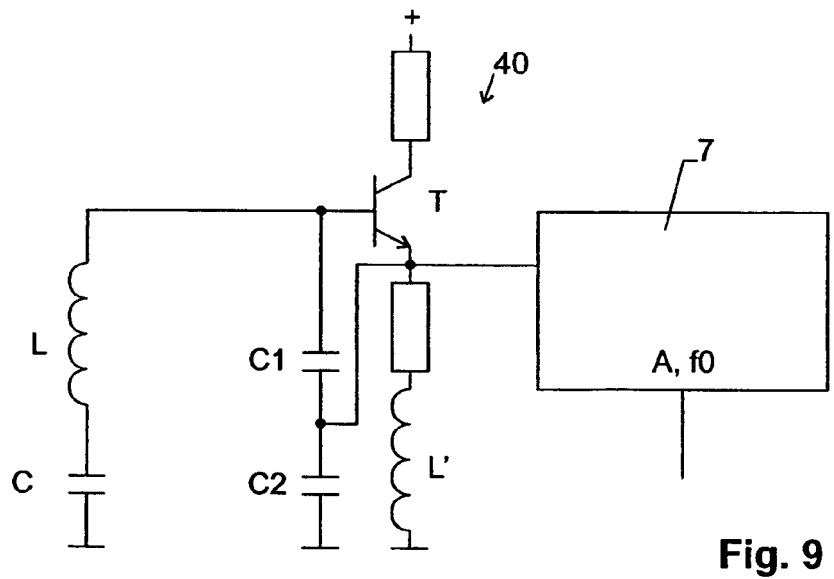

A third embodiment of a circuit is shown in FIG. 9. Here, the capacitor C formed by the electrodes is part of the resonant tank circuit of an active, self-oscillating oscillator 40. The amplitude A and frequency f0 of the output signal of oscillator 40 depend on the capacitance and losses in capacitor C. The corresponding signal is fed to measuring circuit 7, which evaluates the parameters A and f0. Measuring the corresponding parameters A and f0 again allows a sensitive measurement of the desired concentration using calibration data.

In the examples shown so far, the invention was used in a device for qualitatively or quantitatively displaying the concentration a substance (such as glucose) in body liquid. The invention can, however, e.g. also be used in devices that automatically administer medication to a body, such as an insulin pump, where the amount and/or time for administering the medication depends on the measured concentration. It can also be used in any other type of device that requires the measurement of the concentration of a substance in body fluid.

While there are shown and described presently preferred embodiments of the invention, it is to be distinctly understood that the invention is not limited thereto but may be otherwise variously embodied and practiced within the scope of the following claims.

The invention claimed is:

1. A method for determining a concentration of glucose in at least one of an in-vitro and in-viva specimen containing body liquid, the method comprising:
    arranging a first electrode at said specimen, wherein the first electrode is electrically insulated from the specimen by a cover layer, and wherein the first electrode is arranged on a first side of a electrically insulating substrate between the substrate and the cover layer;
    applying a modulated electrical voltage to the first electrode for generating a modulated field in the specimen; and
    measuring at least one parameter depending on a response of the specimen to the field and determining the concentration therefrom,
    wherein the first electrode forms part of a resonant circuit having a resonance frequency and wherein the resonant circuit is operated substantially at the resonance frequency.

2. The method of claim 1 comprising the step of arranging a second electrode at said specimen, wherein the modulated electrical voltage is applied between the first and the second electrode.

3. The method of claim 2 wherein the second electrode is in electric contact with the body liquid in the specimen.

4. The method of claim 1 further comprising the step of measuring a temperature of the specimen and using the temperature to determine the concentration.

5. The method of claim 1 wherein the modulated electrical voltage is a sine voltage.

6. The method of claim 1 wherein the modulated electrical voltage has a frequency between 10 MHz and 2 GHz.

7. The method of claim 6 wherein the modulated electrical voltage has a frequency between 20 MHz and 70 MHz.

8. The method of claim 1 wherein the parameter depends on the electrical impedance at the first electrode.

9. The method of claim 1 wherein the response of the specimen is measured by measuring a signal reflected from the first electrode.

10. The method of claim 1 wherein an antenna electrode is arranged at the specimen in proximity to the first electrode and wherein the response of the specimen is measured by measuring a signal transmitted from the first electrode to the antenna electrode.

11. The method of claim 1 wherein the specimen is a living body.

12. The method of claim 1 comprising the step of using calibration data to convert the parameter to the concentration.

13. The method of claim 1 wherein the resonant circuit is at least part of a tank circuit of an active oscillator and wherein the parameter is at least one of an amplitude and a frequency of a signal generated by the oscillator.

14. The method of claim 1 wherein the modulated voltage is frequency swept from a frequency below the resonance frequency to a frequency above the resonance frequency, and wherein the parameter is at least one of a signal reflected to the first electrode at the resonance frequency and transmitted to an antenna electrode at the resonance frequency.

15. A device for determining a concentration of glucose in at least one of an in-vitro and in-vivo specimen containing body liquid, the device comprising:
    an electrically insulating substrate;
    a first electrode covered by a cover layer of insulating material, wherein the first electrode is arranged on a first side of the substrate between the substrate and the cover layer;
    a signal source connected to the first electrode and configured to apply a modulated electrical voltage to the first electrode to generate an electric field in the specimen;
    a measuring circuit configured to measure at least one parameter depending on a response of the specimen to the field;
    a data processor configured to determine the concentration from the parameter; and
    a second electrode arranged on the substrate, wherein the signal source is connected to and configured to apply the modulated electrical voltage between the first and the second electrodes,
    wherein the second electrode comprises a top electrode layer arranged on the first side of the substrate, said top electrode layer being arranged, at least in part, around the first electrode, and
    wherein the second electrode further comprises a bottom electrode layer arranged on a second side of the substrate, said bottom electrode layer having a larger extension than said top electrode layer.

16. The device of claim 15 comprising a holder for fixing the first electrode to a part of a body with the cover layer facing the body.

17. The device of claim 15, wherein the first electrode is elongate having a width substantially smaller than a length.

18. The device of claim 15 comprising a first and a second signal path between the signal source and the measuring circuit, wherein the first electrode in is arranged in the first signal path and a reference load is arranged in the second signal path, and wherein the measuring circuit is adapted to measure at least one of a relative amplitude and a phase of signals from the first and second signal paths.

19. The device of claim 15 wherein the first electrode is part of a capacitor of a resonant circuit comprising the capacitor and an inductor connected to the signal source.

20. The device of claim 19 wherein the capacitor and the inductor are arranged in series.

21. The device of claim 19 wherein the measuring circuit is configured to measure a voltage over the resonant circuit.

22. The device of claim 19 further comprising an antenna electrode arranged in proximity to the first electrode, wherein the measuring circuit is adapted to measure a signal transmitted from the first electrode to the antenna electrode.

23. A device for determining a concentration of a substance in body liquid of a human body, the device comprising:
- an elongate first electrode having a width substantially smaller than a length;
- a band for fixing the first electrode to at least one of an arm and a leg of a body with a longitudinal axis of the first electrode being substantially parallel to the at least one arm and leg;
- a signal source connected to the first electrode applying a modulated electrical voltage to the first electrode for generating a modulated field in the specimen;
- a measuring circuit for measuring at least one parameter depending on a response of the specimen to the field; and
- a data processor determining the concentration from the parameter.

24. The device of claim 23 further comprising an electrically insulating substrate, wherein the first electrode is arranged on a first side of the substrate between the substrate and the cover layer.

25. The device of claim 23 further comprising a ring electrode extending around the first electrode.

26. The device of claim 25 wherein the ring electrode is connected to a ground.

27. The device of claim 25 wherein the ring electrode surrounds a single strip electrode with the strip electrode forming the first electrode.

* * * * *